(12) United States Patent
Dahlmann et al.

(10) Patent No.: US 7,253,138 B2
(45) Date of Patent: Aug. 7, 2007

(54) CORROSION AND GAS HYDRATE INHIBITORS HAVING IMPROVED WATER SOLUBILITY AND INCREASED BIODEGRADABILITY

(75) Inventors: Uwe Dahlmann, Heidelberg (DE); Michael Feustel, Koengernheim (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 540 days.

(21) Appl. No.: 10/783,724

(22) Filed: Feb. 20, 2004

(65) Prior Publication Data

US 2004/0167040 A1 Aug. 26, 2004

(30) Foreign Application Priority Data

Feb. 24, 2003 (DE) .................. 103 07 725

(51) Int. Cl.
*C10L 1/22* (2006.01)
(52) U.S. Cl. .................. 508/243; 508/244; 508/268
(58) Field of Classification Search ............. 508/243, 508/244, 267
See application file for complete search history.

(56) References Cited

U.S. PATENT DOCUMENTS

| | | | |
|---|---|---|---|
| 3,017,416 A | 1/1962 | Chien-Pen et al. | |
| 3,113,026 A | 12/1963 | Sprung | |
| 3,818,876 A * | 6/1974 | Voogd .................. | 123/25 R |
| 4,161,590 A | 7/1979 | Mueller | |
| 4,171,959 A * | 10/1979 | Vartanian ............... | 44/334 |
| 4,329,239 A * | 5/1982 | Chou .................... | 508/255 |
| 4,493,883 A | 1/1985 | Gruber et al. | |
| 4,730,079 A | 3/1988 | Hofinger et al. .......... | 560/196 |
| 4,997,912 A | 3/1991 | Wirtz et al. ............. | 530/232 |
| 5,135,668 A | 8/1992 | Larsen .................. | 252/8.555 |
| 5,254,138 A | 10/1993 | Kurek ................... | 44/347 |
| 5,439,603 A * | 8/1995 | Carlisle ................ | 508/225 |
| 5,460,728 A | 10/1995 | Klomp et al. ............ | 210/698 |
| 5,648,575 A | 7/1997 | Klomp et al. ............ | 585/15 |
| 5,879,561 A | 3/1999 | Klump et al. | |
| 6,025,302 A | 2/2000 | Pakulski ................ | 507/90 |
| 6,102,986 A | 8/2000 | Klug ................... | 95/153 |
| 6,152,993 A | 11/2000 | Klomp ................. | 95/153 |
| 6,177,497 B1 | 1/2001 | Klug et al. .............. | 524/376 |
| 6,261,346 B1 | 7/2001 | Breuer et al. ............ | 106/14.15 |
| 6,369,004 B1 | 4/2002 | Klug et al. .............. | 507/90 |
| 6,372,918 B1 | 4/2002 | Feustel et al. ........... | 548/349.1 |
| 6,379,294 B1 | 4/2002 | Buijs et al. ............. | 584/114 |
| 2003/0013614 A1 | 1/2003 | Klug et al. .............. | 507/200 |
| 2004/0030206 A1 | 2/2004 | Dahlmann et al. ......... | 585/15 |

FOREIGN PATENT DOCUMENTS

| | | |
|---|---|---|
| CA | 2 104 505 | 2/1994 |
| DE | 199 30 683 | 1/2001 |
| DE | 100 59 816 | 4/2002 |
| DE | 101 14 638 | 5/2002 |
| EP | 0 212 265 | 3/1987 |
| EP | 0 320 769 | 6/1989 |
| EP | 0 446 616 | 9/1991 |
| EP | 0 473 229 | 3/1992 |
| EP | 0 584 711 | 3/1994 |
| EP | 0 736 130 | 10/1996 |
| EP | 0 824 631 | 2/1998 |
| EP | 0 914 407 | 5/1999 |
| EP | 0 946 788 | 10/1999 |
| JP | 05193073 A * | 8/1993 |
| WO | WO 98/23792 | 6/1998 |
| WO | WO 99/13197 | 3/1999 |
| WO | WO 00/78706 | 12/2000 |

(Continued)

OTHER PUBLICATIONS

Chevron Quality Gas: Ask The expert, posted to the web on or before Jun. 25, 2001 (see date in URL). Retrieved from the internet at <http://web.archive.org/web/20010625104005/http://www.chevron.com/prodserv/fuels/techrongas/faq.shtml>.*
Database Chemcats-Online, Interchim Intermediates, XP-002285322, Jul. 9, 2002, Montlucon, Cedex, France.
Patent Abstracts of Japan—JP 5193073, (Aug. 3, 1993).
SL Shapiro, et al., "Aminoalkyamides and Oxazolidinediones", J. of Amer Chem Soc., pp. 3083-3088, vol. 81, No. 12, (1959).

(Continued)

*Primary Examiner*—Vasu Jagannathan
*Assistant Examiner*—James C. Goloboy
(74) *Attorney, Agent, or Firm*—Richard P. Silverman

(57) ABSTRACT

The invention provides the compounds of the formula (1)

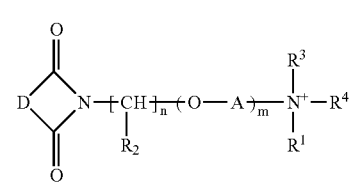

(1)

where
$R^1$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$,
$R^2$ is hydrogen —$CH_3$ or —OH,
$R^3$, $R^4$ are each independently $C_1$- to $C_{22}$-alkyl, $C_2$- to $C_{22}$-alkenyl, $C_6$- to $C_{30}$-aryl or $C_7$- to $C_{30}$-alkylaryl,
$R^5$ is hydrogen, $C_1$- to $C_{22}$-alkyl or $C_2$- to $C_{22}$-alkenyl,
A is a $C_2$- to $C_4$-alkylene group,
D is a $C_2$- to $C_5$-alkylene group which may contain one or two heteroatoms,
m is a number from 0 to 30,
n is a number from 1 to 18,
and also their use as corrosion and gas hydrate inhibitors.

8 Claims, No Drawings

FOREIGN PATENT DOCUMENTS

WO          WO 01/09082          2/2001

OTHER PUBLICATIONS

LM Werbel, et al., "Antischistosomal Effects of 5-(2,4,5-Trichlorophenyl) Hydantoin and Related Compounds", J. of Medicinal Chem, vol. 20, No. 12, pp. 1569-1572, (1977).

C Lion, et al., "Synthese De Nouveaux Initiateurs . . . ", Phosphorous, Sulfur and Silicon, vol. 161, pp. 97-113, (2000) Amsterdam, NV.

L Cekuoliene, "Aminimethylation of (+−)-1,2,-BIS(3,5-Dioxopiperazin-1-YL)Propane", Lietuvos TSR Mokslu, vol. 5, pp. 41-45, (1986).

Messinger et al., "Notes on the Synthesis of Alpha-Aminosulfones and Alpha-Amidosulfones", Archiv Der Pharmazie, vol. 307, No. 8, pp. 653-655 (1974).

\* cited by examiner

CORROSION AND GAS HYDRATE INHIBITORS HAVING IMPROVED WATER SOLUBILITY AND INCREASED BIODEGRADABILITY

The present invention relates to an additive and to a process for corrosion inhibition and gas hydrate inhibition on and in equipment for extracting and transporting hydrocarbons in crude oil extraction and processing.

In industrial processes in which metals come into contact with water or else with biphasic oil-water systems, there is the risk of corrosion. This is particularly marked when the aqueous phase, as in the case of crude oil production and processing operations, has a high salt content or, as a result of dissolved acidic gases such as carbon dioxide or hydrogen sulfide, is acidic. It is therefore not possible to exploit a deposit and to process crude oil without special additives to protect the equipment used.

Although suitable corrosion protectors for crude oil extraction and processing have been known for some time, they will become unacceptable for offshore applications in the future for reasons of environmental protection.

As typical prior art corrosion inhibitors, amides, amido amines and imidazolines of fatty acids and polyamines have extremely good oil solubility and are therefore only present in the corrosive aqueous phase in low concentration as a consequence of poor partitioning equilibria. Accordingly, these products have to be used in high dosage despite their poor biodegradability.

DE-A-199 30 683 describes corresponding amido amines/imidazolines which are obtained by reacting alkylpolyglycol ether carboxylic acids with polyamines and which, as a consequence of better partitioning, can be used in low concentrations.

Quaternary alkylammonium compounds (quats) constitute alternative prior art corrosion protectors which have not only corrosion-inhibiting but also biostatic properties. Despite improved water solubility, the quats, in comparison to the imidazolines for example, exhibit distinctly reduced film persistence and therefore likewise lead to effective corrosion protection only in high dosage. The strong algae toxicity and the moderate biodegradability restrict the use of quats ever more to ecologically insensitive fields of application, for example onshore.

EP-B-0 946 788 describes a process for protecting metal surfaces against corrosion using ester quats which, it is disclosed, have good biodegradability and low aquatic toxicity.

EP-A-0 320 769 discloses optionally quaternized fatty acid esters of oxyalkylated alkylamino alkylenamines and their use as corrosion inhibitors.

EP-B-0 212 265 describes quaternary polycondensates of alkoxylated alkylamines and dicarboxylic acids and their use as corrosion inhibitors and demulsifiers in crude oils.

EP-B-0 446 616 describes ampholytes and betaines based on fatty acid amido alkylamines which have very good corrosion protection and significantly reduced algae toxicity under the given test conditions.

EP-B-0 584 711 discloses esters, amides and imides of alkenylsuccinic acids with alkoxyalkylamines and their metal or ammonium salts as emulsifiers and corrosion inhibitors for metalworking assistants. The use of alkenylsuccinic esters or amido amine quats or corresponding betaines is not described.

Gas hydrates are crystalline inclusion compounds of gas molecules in water which form under certain temperature and pressure conditions (low temperature and high pressure). The water molecules form cage structures around the appropriate gas molecules. The lattice structure formed from the water molecules is thermodynamically unstable and is always stabilized by the incorporation of gas molecules. Depending on pressure and gas composition, these icelike compounds can exist even to above the freezing point of water (up to above 25° C.).

In the crude oil and natural gas industry, great significance attaches in particular to the gas hydrates which form from water and the natural gas constituents methane, ethane, propane, isobutane, n-butane, nitrogen, carbon dioxide and hydrogen sulfide. Especially in modem natural gas extraction, the existence of these gas hydrates constitutes a great problem, especially when wet gas or multiphasic mixtures of water, gas and alkane mixtures are subjected to low temperatures under high pressure. As a consequence of their insolubility and crystalline structure, the formation of gas hydrates leads here to the blockage of a wide variety of extraction equipment such as pipelines, valves or production equipment in which wet gas or multiphasic mixtures are transported over long distances, as occurs especially in colder regions of the earth or on the seabed.

In addition, gas hydrate formation can also lead to problems in the course of the drilling operation to develop new gas or crude oil deposits at the appropriate pressure and temperature conditions by the formation of gas hydrates in the drilling fluids.

In order to prevent such problems, gas hydrate formation in gas pipelines, in the course of transport of multiphasic mixtures or in drilling fluids, can be suppressed by using relatively large amounts (more than 10% by weight, based on the weight of the aqueous phase) of lower alcohols such as methanol, glycol or diethylene glycol. The addition of these additives has the effect that the thermodynamic limit of gas hydrate formation is shifted to lower temperatures and higher pressures (thermodynamic inhibition). However, the addition of these thermodynamic inhibitors causes serious safety problems (flashpoint and toxicity of the alcohols), logistical problems (large storage tanks, recycling of these solvents) and accordingly high costs, especially in offshore extraction.

Attempts are therefore being made today to replace thermodynamic inhibitors by adding additives in amounts of <2% in temperature and pressure ranges in which gas hydrates can form. These additives either delay gas hydrate formation (kinetic inhibitors) or keep the gas hydrate agglomerates small and therefore pumpable, so that they can be transported through the pipeline (agglomerate inhibitors or antiagglomerates). The inhibitors used either prevent nucleation and/or the growth of the gas hydrate particles, or modify the hydrate growth in such a way that relatively small hydrate particles result.

The gas hydrate inhibitors which have been described in the patent literature, in addition to the known thermodynamic inhibitors, are a multitude of monomeric and also polymeric substance classes which are kinetic inhibitors or agglomeration inhibitors. Of particular significance in this context are polymers having a carbon backbone which contain both cyclic (pyrrolidone or caprolactam radicals) and acyclic amide structures in the side groups.

EP-B-0 736 130 discloses a process for inhibiting gas hydrates which entails feeding a substance of the formula

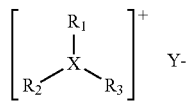

where X=S, N—$R_4$ or P—$R_4$, $R_1$, $R_2$ and $R_3$=alkyl having at least 4 carbon atoms, $R_4$=H or an organic radical, and Y=anion.

This therefore includes compounds of the formula

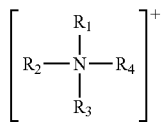

where $R_4$ may be any desired radical, but the $R_1$ to $R_3$ radicals have to be alkyl radicals having at least 4 carbon atoms.

EP-B-0 824 631 discloses a process for inhibiting gas hydrates which entails feeding a substance of the formula

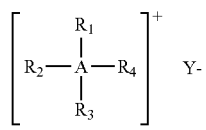

where $R_1$, $R_2$=linear/branched alkyl radicals having 4 or 5 carbon atoms, $R_3$, $R_4$=organic radicals having at least 8 carbon atoms and A=nitrogen or phosphorus. $Y^-$ is an anion. Two of the $R_1$ to $R_4$ radicals have to be linear or branched alkyl radicals having 4 or 5 carbon atoms.

U.S. Pat. No. 5,648,575 discloses a process for inhibiting gas hydrates. The process comprises the use of a compound of the formula

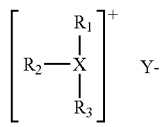

where $R^1$, $R^2$ are linear or branched alkyl groups having at least 4 carbon atoms, $R^3$ is an organic radical having at least 4 atoms, X is sulfur, $NR^4$ or $PR^4$, $R^4$ is hydrogen or an organic radical, and Y is an anion. The document discloses only those compounds which have at least two alkyl radicals having at least 4 carbon atoms.

U.S. Pat. No. 6,025,302 discloses polyetheramine ammonium compounds as gas hydrate inhibitors whose ammonium nitrogen atom, in addition to the polyetheramine chain, bears 3 alkyl substituents.

WO-99/13197 discloses ammonium compounds as gas hydrate inhibitors which have at least one alkoxy group esterified with alkylcarboxylic acids. The advantages of using alkenylsuccinic acid derivatives are not disclosed.

WO-01/09082 discloses a process for preparing quaternary amines which, however, bear no alkoxy groups, and their use as gas hydrate inhibitors.

WO-00/078 706 discloses quaternary ammonium compounds as gas hydrate inhibitors which, however, bear no carbonyl radicals.

EP-B-914407 discloses the use of trisubstituted amine oxides as gas hydrate inhibitors.

U.S. Pat. No. 5,254,138 discloses detergent additives for diesel fuel, said additives comprising polyamine derivatives of succinimide.

It is an object of the present invention to find novel corrosion inhibitors which, coupled with equally good or improved corrosion protection, offer not only optimum water solubility, more rapid film formation and therefore improved film persistence, but also improved biodegradability in comparison to the prior art corrosion inhibitors.

It is a further object of the present invention to find improved additives which not only slow the formation of gas hydrates (kinetic inhibitors) but also keep gas hydrate agglomerates small and pumpable (antiagglomerates), in order to thus ensure a broad spectrum of application with a high action potential. In addition, it should be possible to replace the thermodynamic inhibitors used currently (methanol and glycols) which cause considerable safety problems and logistical problems.

Prior art gas hydrate inhibitors are commonly coadditivized with corrosion inhibitors, in order to prevent corrosion of the transport and extraction equipment. As a consequence of the frequent lack of immediate compatibility of gas hydrate inhibitor and corrosion protector in the course of formulation, there is additional work for the user. It would be a significant advantage over the prior art if coadditivization with corrosion inhibitors were no longer obligatory.

It has now been found that, surprisingly, quaternary alkylaminoalkyl/alkoxy imides of dicarboxylic acids exhibit excellent action as corrosion inhibitors and gas hydrate inhibitors, and also improved film persistence and good biodegradability.

The present invention therefore provides compounds of the formula (1)

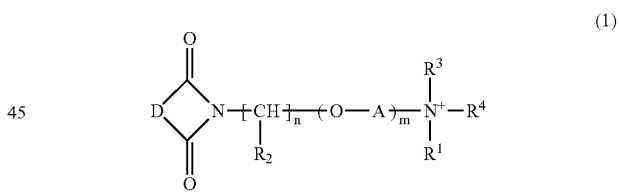

where
- $R^1$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$,
- $R^2$ is hydrogen —$CH_3$ or —OH,
- $R^3$, $R^4$ are each independently $C_1$- to $C_{22}$-alkyl, $C_2$- to $C_{22}$-alkenyl, $C_6$- to $C_{30}$-aryl or $C_7$- to $C_{30}$-alkylaryl,
- $R^5$ is hydrogen, $C_1$- to $C_{22}$-alkyl or $C_2$- to $C_{22}$-alkenyl,
- A is a $C_2$- to $C_4$-alkylene group,
- D is a $C_2$- to $C_5$-alkylene group which may contain one or two heteroatoms,
- m is a number from 0 to 30,
- n is a number from 1 to 18.

The invention further provides a method for inhibiting corrosion on metal surfaces, in particular ferrous surfaces, by adding at least one compound of the formula (1) to a corrosive system which is in contact with the metal surfaces.

The invention further provides a method for inhibiting gas hydrates by adding at least one compound of the formula (1) to a system of water and hydrocarbons which tends to the formation of gas hydrates.

The invention further provides the use of compounds of the formula 1 as corrosion inhibitors and gas hydrate inhibitors.

For the purposes of this invention, corrosive systems are preferably liquid/liquid or liquid/gaseous multiphase systems comprising water and hydrocarbons which comprise corrosive constituents, such as salts and acids, in free and/or dissolved form. The corrosive constituents may also be gaseous, for instance hydrogen sulfide and carbon dioxide.

For the purposes of this invention, hydrocarbons are organic compounds which are constituents of the crude oil/natural gas, and their secondary products. For the purposes of this invention, hydrocarbons are also volatile hydrocarbons, for example methane, ethane, propane, butane. For the purposes of this invention, they also include the further gaseous constituents of crude oil/natural gas, for instance hydrogen sulfide and carbon dioxide.

$R^1$, $R^3$ and $R^4$ are preferably each independently an alkyl or alkenyl group of from 1 to 14 carbon atoms, in particular those groups having from 1 to 6 carbon atoms and especially methyl or butyl groups.

Where $R^1$ is $C_1$- to $C_{22}$-alkyl, $C_2$- to $C_{22}$-alkenyl, $C_6$- to $C_{30}$-aryl or $C_7$- to $C_{30}$-alkylaryl, counterions for the compounds of the formula (1) are all anions which do not impair the solubility of the compounds of the formula (1) in the organic-aqueous mixed phases. Such counterions are, for example, methylsulfate ions (methosulfate) or halide ions.

Where $R^1$ is —$CHR^5$—$COO^-$ or —$O^-$ radicals, compounds of the formula (1) are betaines and amine oxides respectively and, as internal salts (ampholytes), have an intramolecular counterion.

$R^2$ and $R^5$ are preferably each hydrogen. m is preferably a number between 1 and 30, in particular between 2 and 12, especially 3 and 6.

n is preferably a number between 2 and 12, in particular from 3 to 6.

A may be straight-chain or branched and is preferably an ethylene or propylene group, in particular an ethylene group. The alkoxy groups denoted by $(O-A)_m$ may also be mixed alkoxy groups.

D provides a ring closure between the carbonyl groups of formula 1. The ring size including the carbonyl carbon atoms and the nitrogen atom is in the range from 5 to 8 ring atoms. D is therefore an alkylene group which contains from 2 to 5 carbon atoms and may contain one or two heteroatoms.

D may bear an $R^6$ substituent at any position.

$R^6$ may be a desired organic radical which contains from 1 to 300 carbon atoms and which may contain heteroatoms. When $R^6$ contains no heteroatoms, it is preferably $C_1$- to $C_{100}$-alkyl or $C_2$- to $C_{100}$-alkenyl radicals which are oligomers derived from $C_2$- to $C_8$-alkylene building blocks, in particular from ethylene, propylene and butylene.

When $R^6$ is alkyl or alkenyl radicals, these may be straight-chain or branched, preferably branched. In a particular embodiment, the branched alkyl or alkenyl radicals are polypropylene or polyisobutylene having more than 12 carbon atoms.

When $R^6$ contains heteroatoms, they are preferably nitrogen or oxygen atoms or both, preferably both. Nitrogen atoms may be present in quaternized form.

$R^6$ is preferably a radical of the formula (2)

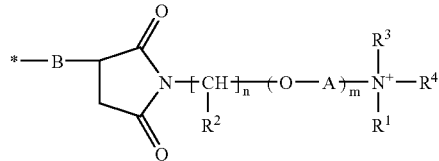

where
B is a $C_1$- to $C_{100}$-alkylene or $C_2$- to $C_{100}$-alkenylene radical which is an oligomer derived from $C_2$- to $C_8$-alkylene building blocks, in particular from ethylene, propylene and butylene, and the bond D in formula (1) is via a free valence of an alkyl group at any desired point on B.

$R^1$, $R^2$, $R^3$, $R^4$, m and n are each as already defined above with the areas of preference specified above in each case for $R^1$, $R^2$, $R^3$, $R^4$, m and n.

The compounds according to the invention can be used alone or in combination with other known corrosion inhibitors and/or gas hydrate inhibitors. In general, sufficient corrosion inhibitor and/or gas hydrate inhibitor according to the invention is used to obtain sufficient corrosion protection and protection from gas hydrate formation under the given conditions.

Preferred use concentrations of the corrosion inhibitors based on the pure compounds of the invention are from 5 to 5000 ppm, preferably from 10 to 1000 ppm, in particular from 15 to 150 ppm.

The gas hydrate inhibitors are generally used in amounts between 0.01 and 5% by weight of the pure compounds according to the invention based on the aqueous phase, preferably between 0.05 and 2% by weight.

Also particularly suitable as corrosion inhibitors and/or gas hydrate inhibitors are mixtures of the products according to the invention with other corrosion inhibitors and/or gas hydrate inhibitors known from the literature.

Particularly suitable corrosion inhibitors and therefore a preferred embodiment of this invention are mixtures of the compounds of the formula (1), such as those comprising amido amines and/or imidazolines of fatty acids and polyamines and their salts, quaternary ammonium salts, alkylpyridines, ethoxylated/propoxylated amines, amphoglycinates and -propionates, betaines or compounds described in DE-A-199 30 683.

Particularly suitable gas hydrate inhibitors and therefore a preferred embodiment of this invention are mixtures of the compounds of the formula (1) with one or more polymers having a carbon backbone obtained by polymerization and amide bonds in the side chains. These include in particular homopolymers and/or copolymers of vinylpyrrolidone, vinylcaprolactam, isopropylacrylamide, acryloylpyrrolidine, N-methyl-N-vinylacetamide and also further anionic, cationic and neutral comonomers having a vinylic double bond.

When mixtures are used, the concentration ratios between the gas hydrate inhibitors according to the invention and the mixed-in components are from 90:10 to 10:90 percent by weight, and preference is given to mixtures in the ratios from 75:25 to 25:75, and in particular from 60:40 to 40:60.

The compounds according to the invention can be prepared by condensing dicarboxylic acid derivatives, for example alkenylsuccinic anhydrides, with tertiary alkylaminoalkyl/alkoxy amines to give the corresponding dicarboximides. Subsequently, quaternization is effected using suitable alkylating agents.

The preparation of alkenylsuccinic anhydrides by thermal or catalyzed "ene" reaction is described in the prior art. In this reaction, olefins, preferably olefins having a terminal double bond, are reacted with maleic anhydride under elevated temperatures. Depending on the reaction method, on the type of the olefin used and on the molar ratio used, mono- and/or bisadducts, in some cases polyadducts, are obtained.

The tertiary alkylaminoalkyl/alkoxy amines used are preferably based on alkylenediamines having $C_1$- to $C_{22}$-alkyl radicals or $C_2$- to $C_{22}$-alkenyl radicals, preferably $C_1$- to $C_8$-dialkylaminoalkylenamines. Particularly suitable dialkylaminoalkylenamines are, for example, N,N-dibutylaminopropylamine, N,N-diethylaminopropylamine, N,N-dimethylaminopropylamine, N,N-dimethylaminobutylamine, N,N-dimethylaminohexylamine, N,N-dimethylaminodecylamine, N,N-dibutylaminoethylamine and N,N-dimethylamino-2-hydroxypropylamine.

The alkenylsuccinic anhydrides are generally reacted with the alkylene-diamines in such a way that there is complete condensation to the alkenylsuccinimide with elimination of water of reaction. The degree of conversion can be followed via determination of the acid number and/or via determination of the basic nitrogen. The reaction is done at 60-200° C., preferably at 120-160° C., in order to ensure very substantially complete conversion. The process-dependent formation of corresponding amines as inevitable by-products and the secondary products resulting from them are included.

The reaction proceeds without solvent, but can also preferably be carried out in solution. Especially when high conversions and low acid numbers of the resulting alkenylsuccinimides are pursued, it is necessary to use solvents. Suitable solvents for the preparation are organic compounds which azeotropically remove the water of reaction. In particular, aromatic solvents or solvent mixtures, or alcohols, can be used. Particular preference is given to 2-ethylhexanol. The reaction is then effected at the boiling point of the azeotrope.

For the preparation of the quats according to the invention, the alkenylsuccinimidoalkylamines are quaternized in a subsequent reaction step. The quaternization may be effected by appropriate alkylating agents at from 50 to 150° C. Suitable alkylating agents are alkyl halides and alkyl sulfates, preferably methyl chloride, methyl iodide, butyl bromide and dimethyl sulfate.

For the preparation of the betaines according to the invention, the alkenylsuccinimidoalkylamines are reacted in a subsequent reaction step with a halocarboxylic acid and a base, preferably chloroacetic acid and sodium hydroxide. This may be effected by initially charging the alkenylsuccinimidoalkylamines with from 50 to 125 mol % of halocarboxylic acid at 40° C. and reacting at from 40 to 100° C. by adding the base and the amount remaining up to 125 mol % of halocarboxylic acid, all at once or in portions.

The basic compounds used may be alkali metal/alkaline earth metal hydroxides or alkoxides (sodium methoxide, sodium ethoxide, potassium tert-butoxide), but preferably alkali metal hydroxides, particularly sodium hydroxide or potassium hydroxide, in particular their aqueous solutions.

The amine oxides according to the invention are prepared by existing prior art processes, preferably by oxidation of the appropriate tertiary amine group with peroxides or peracids, preferably with hydrogen peroxide.

The reaction to give the compounds according to the invention is preferably effected in solution, but can also be carried out without solvent. Suitable solvents for the preparation of quats, betaines or amine oxides are inert alcohols such as isopropanol, or inert ethers such as tetrahydrofuran, glyme, diglyme and MPEGs.

Depending on the given requirements, the solvent used may remain in the product according to the invention or has to be removed distillatively.

EXAMPLES a) General Method for the Preparation of the Alkenylsuccinimidoalkylamines A stirred apparatus equipped with distillation head with condenser was initially charged with 2.5 mol of the appropriate alkenylsuccinic anhydride (based on hydrolysis number) with nitrogen purging and heated to 60° C. 2.5 mol of the appropriate alkylendiamine were then added dropwise over 2 hours, in which time the reaction mixture heated to approx. 100° C. The reaction mixture was stirred at 100° C. for a further 1 h and then the reaction temperature was continuously increased from 100° C. to 160° C. over a period of 8 hours, in which time water of reaction distilled off. Finally, reaction was continued at 160° C. for 4 hours.

Example 1 (Dodecenyl-/tetradecenylsuccinimido-N, N-dimethylpropylamine)

671 g of dodecenyl-/tetradecenylsuccinic anhydride (HN=418.1 mg KOH/g) and 255.5 g of dimethylaminopropylamine (DMAPA) were used to obtain 875 g of dodecenyl-/tetradecenylsuccinimido-N,N-dimethylpropylamine having AV=3.2 mg KOH/g and basic N=4.03%.

Example 2 (Tetrapropylenesuccinimido-N,N-dimethylpropylamine)

732.0 g of tetrapropylenesuccinic anhydride (HN=383.3 mg KOH/g) and 255.5 g of dimethylaminopropylamine (DMAPA) were used to obtain 945 g of tetrapropylenesuccinimido-N,N-dimethylpropylamine having AV=10.3 mg KOH/g and basic N=3.73%.

Example 3 (Pentapropylenesuccinimido-N,N-dimethylpropylamine)

978.5 g of pentapropylenesuccinic anhydride (HN=286.7 mg KOH/g) and 255.5 g of dimethylaminopropylamine (DMAPA) were used to obtain 1181 g of pentapropylenesuccinimido-N,N-dimethylpropylamine having AN=15.1 mg KOH/g and basic N=2.87%.

Example 4 (Polyisobutenylsuccinimido-N,N-dimethylpropylamine)

978.3 g of polyisobutenylsuccinic anhydride (based on PIB 300; HN=286.8 mg KOH/g) and 255.5 g of dimethylaminopropylamine (DMAPA) were used to obtain 1 180 g of polyisobutenylsuccinimido-N,N-dimethylpropylamine having AV=9.7 mg KOH/g and basic N=2.96%.

Example 5 (Polyisobutenylsuccinimido-N,N-dimethylpropylamine)

1 310 g (2 mol) of polyisobutenylsuccinic anhydride (based on PIB 550; HN=171.3 mg KOH/g) and 204.0 g (2 mol) of dimethylaminopropylamine (DMAPA) were used to obtain 1 468 g of polyisobutenylsuccinimido-N,N-dimethylpropylamine having AN=6.7 mg KOH/g and basic N=1.89%.

Example 6 (Polyisobutenylsuccinimido-N,N-dimethylpropylamine)

870.3 g (2 mol) of polyisobutenylsuccinic anhydride (based on PIB 550; HN=257.9 mg KOH/g) and 204.0 g (2 mol) of dimethylaminopropylamine (DMAPA) were used to obtain 1 468 g of polyisobutenylsuccinimido-N,N-dimethylpropylamine having AN=15.4 mg KOH/g and basic N=2.69%.

b) General Method for the Preparation of the Succinimidoammonium Betaines

A stirred apparatus was initially charged with 2 mol (based on basic N) of the appropriate alkenylsuccinimidoalkylamine with nitrogen purging and dissolved in 40% by weight of isopropanol (based on the total amount) at 40° C. with continuous stirring. 2.5 mol of monochloroacetic acid were then added in one portion and stirred homogeneously. Subsequently, 2.7 mol of an aqueous NaOH solution (216 g of a 50% solution) were added in 4 portions to this reaction mixture. The addition was such that the internal temperature did not exceed 60° C. (in some cases, cooling was necessary). After each addition, reaction was continued at 80° C. in each case for 30 minutes, and for 4 hours at the end. Subsequently, the precipitated NaCl residue was removed by means of a pressure filter press through Seitz T 5500.

Example 7 (Dodecenyl-/tetradecenylsuccinimido-N, N-dimethylpropylammonium N-methylcarboxyl betaine)

695.3 g of dodecenyl-/tetradecenylsuccinimido-N,N-dimethylpropylamine (basic N=4.03%) and 236.3 g of monochloroacetic acid (MCAA) were used to obtain 1 600 g of dodecenyl-/tetradecenylsuccinimido-N, N-dimethylpropylammonium N-methylcarboxyl betaine (AS content approx. 54%, approx. 6% water, approx. 40% isopropanol).

Example 8 (Tetrapropylenesuccinimido-N,N-dimethylpropylammonium N-methylcarboxyl betaine)

751.2 g of tetrapropylenesuccinimido-N,N-dimethylpropylamine (basic N=3.73%) and 236.3 g of monochloroacetic acid (MCAA) were used to obtain 1 710 g of tetrapropylenesuccinimido-N,N-dimethylpropylammonium N-methylcarboxyl betaine (AS content approx. 54%, approx. 6% water, approx. 40% isopropanol).

Example 9 (Pentapropylenesuccinimido-N,N-dimethylpropylammonium N-methylcarboxyl betaine)

976.3 g of pentapropylenesuccinimido-N,N-dimethylpropylamine (basic N=2.87%) and 236.3 g of monochloroacetic acid (MCAA) were used to obtain 2 080 g of pentapropylenesuccinimido-N,N-dimethylpropylammonium N-methylcarboxyl betaine (AS content approx. 54%, approx. 6% water, approx. 40% isopropanol).

Example 10 (Polyisobutenylsuccinimido-N,N-dimethylpropylammonium N-methyl-carboxyl betaine)

946.0 g of polyisobutenylsuccinimido-N,N-dimethylpropylamine (based on PIB 300; basic N=2.96%) and 236.3 g of monochloroacetic acid (MCAA) were used to obtain 2 035 g of polyisobutenylsuccinimido-N,N-dimethylpropylammonium N-methyl-carboxyl betaine (AS content approx. 54%, approx. 6% water, approx. 40% isopropanol).

Example 11 (Polyisobutenylsuccinimido-N,N-dimethylpropylammonium N-methyl-carboxyl betaine)

741 g (1 mol) of polyisobutenylsuccinimido-N,N-dimethylpropylamine (based on PIB 550; basic N=1.89%) and 118.2 g (1.25 mol of monochloroacetic acid (MCAA) were used to obtain 1 415 g of polyisobutenylsuccinimido-N,N-dimethyl-propyl-ammonium N-methylcarboxyl betaine (AS content approx. 54%, approx. 6% water, approx. 40% isopropanol).

Example 12 (Polyisobutenylsuccinimido-N,N-dimethylpropylammonium N-methyl-carboxyl betaine)

520.8 g (1 mol) of polyisobutenylsuccinimido-N,N-dimethylpropylamine (based on PIB 550; basic N=2.69%) and 118.2 g (1.25 mol of monochloroacetic acid (MCAA) were used to obtain 1 090 g of polyisobutenylsuccinimido-N,N-dimethylpropyl-ammonium N-methylcarboxyl betaine (AS content approx. 54%, approx. 6% water, approx. 40% isopropanol).

Effectiveness of the compounds according to the invention as corrosion inhibitors The compounds according to the invention were tested as corrosion inhibitors in the Shell wheel test. Coupons of carbon steel (DIN 1.1203 having 15 cm$^2$ surface area) were immersed in a salt water/petroleum mixture (9:1.5% NaCl solution, adjusted to pH 3.5 using acetic acid) and subjected to this medium at a rotation rate of 40 rpm at 70° C. for 24 hours. The dosage of the inhibitor was 50 ppm of a 40% solution of the inhibitor. The protection values were calculated from the mass reduction of the coupons, based on a blank value.

In the table which follows, "comparison" refers to a commercial soya fatty acid amidopropyl-N,N-dimethylammonium carboxymethyl betaine described by EP-B-0 446 616 (prior art corrosion inhibitor).

TABLE 1

| | (SHELL wheel test) | |
|---|---|---|
| Example | Corrosion inhibitor tel quel | ø Protection % |
| Comparison | | 75.4 |
| 13 | Betaine from example 7 | 84.9 |
| 14 | Betaine from example 8 | 84.0 |
| 15 | Betaine from example 9 | 90.4 |
| 16 | Betaine from example 10 | 90.1 |
| 17 | Betaine from example 11 | 80.6 |
| 18 | Betaine from example 12 | 82.7 |

The products were also tested in the LPR test (test conditions similar to ASTM D 2776).

TABLE 2

(LPR test)

| | | Protection after [%] | | |
|---|---|---|---|---|
| Example | Corrosion inhibitor | 10 min | 30 min | 60 min |
| Comparison | | 45.9 | 59.2 | 64.2 |
| 19 | Betaine from example 7 | 72.5 | 92.0 | 98.1 |
| 20 | Betaine from example 8 | 74.0 | 81.3 | 84.9 |
| 21 | Betaine from example 9 | 77.9 | 94.0 | 99.8 |
| 22 | Betaine from example 10 | 79.1 | 92.3 | 99.2 |
| 23 | Betaine from example 11 | 61.9 | 70.6 | 80.6 |
| 24 | Betaine from example 12 | 70.0 | 79.4 | 86.3 |

As can be seen from the above test results, the products according to the invention have very good corrosion protection properties at low dosage and exceed the performance of the prior art inhibitors.

The foam properties were tested with the agitation foam method. To this end, 50 ml of a 3% aqueous solution of the appropriate corrosion inhibitor in demineralized water were agitated in a closed 100 ml measuring cylinder 20 times within 10 sec. On completion of the agitation, the foaming behavior was assessed using the total volume of the solution (foam height) and the foam decomposition time (time until attainment of the starting volume of 50 ml). In general, this testing method is of moderate reproducibility, but is outstandingly suited to assessing the trend of the foaming behavior into weakly foaming, foaming or strongly foaming.

TABLE 3

(Agitation foam)

| Example | Corrosion inhibitor | Foaming behavior |
|---|---|---|
| Comparison | | Strongly foaming |
| 25 | Betaine from example 7 | Foaming |
| 26 | Betaine from example 8 | Foaming |
| 27 | Betaine from example 9 | Weakly foaming |
| 28 | Betaine from example 10 | Weakly foaming |
| 29 | Betaine from example 11 | Weakly foaming |
| 30 | Betaine from example 12 | Foaming |

The compounds are biodegradable and have better foaming behavior than the prior art corrosion inhibitors.

The following abbreviations have been used:
AN=acid value (alternatively "acid number")
HN=saponification value (alternatively "saponification number")
OHN=hydroxyl value (alternatively "hydroxyl number")
AS content=content of active matter

What is claimed is:

1. A compound of the formula (1)

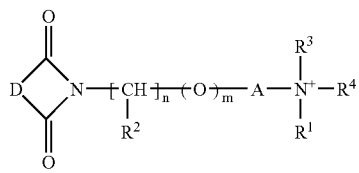

(1)

where $R^1$ is selected from the group consisting of $C_1$- to $C_{22}$-alkyl, $C_2$- to $C_{22}$-alkenyl, $C_6$- to $C_{30}$-aryl, $C_7$- to $C_{30}$-alkylaryl, —$CHR^5$—$COO^-$, and —$O^-$, $R^2$ is hydrogen, —$OH_3$ or —OH, $R^3$, $R^4$ are each independently $C_1$- to $C_{22}$-alkyl, $C_2$- to $C_{22}$-alkenyl, $C_6$- to $C_{30}$-aryl or $C_7$- to $C_{30}$-alkylaryl, $R^5$ is hydrogen, $C_1$- to $C_{22}$-alkyl or $C_2$- to $C_{22}$-alkenyl, A is a $C_2$- to $C_4$-alkylene group, D is a $C_2$- to $C_5$-alkylene group, m is a number from 1 to 30, n is a number from 1 to 18.

2. The compound as claimed in claim 1, wherein $R^3$ and $R^4$ are each an alkyl or alkenyl group having from 1 to 14 carbon atoms.

3. The compound as claimed in claim 1, wherein $R^2$ is hydrogen.

4. The compound as claimed in claim 1, wherein n is a number in the range from 2 to 12.

5. The compound as claimed in claim 1, wherein D includes an $R^6$ radical which is a $C_1$- to $C_{100}$-alkyl or a $C_2$- to $C_{100}$-alkenyl radical which is an oligomer of $C_2$- to $C_8$-alkylenes.

6. The compound as claimed in claim 1, wherein D includes an $R^6$ radical which includes a hetero atom selected from the group consisting of nitrogen, oxygen, and mixtures thereof.

7. The compound as claimed in claim 1, wherein D includes an $R^6$ radical of formula 2

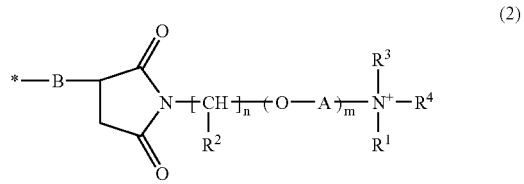

(2)

where

B is a $C_1$- to $C_{100}$-alkylene or a $C_2$- to $C_{100}$-alkenylene radical which is an oligomer of $C_2$- to $C_8$-alkylene building blocks and B is bonded to D via a free valence of an alkyl group at any point on B.

8. A method for inhibiting corrosion and gas hydrate formation, said method comprising adding to a mixture of hydrocarbon and water the compound of claim 1 in amounts of from 5 to 5 000 ppm.

* * * * *

UNITED STATES PATENT AND TRADEMARK OFFICE
CERTIFICATE OF CORRECTION

PATENT NO. : 7,253,138 B2
APPLICATION NO. : 10/783724
DATED : August 7, 2007
INVENTOR(S) : Dahlmann et al.

It is certified that error appears in the above-identified patent and that said Letters Patent is hereby corrected as shown below:

In Column 11, lines 53-58, Claim 1, replace formula (1) with the following:

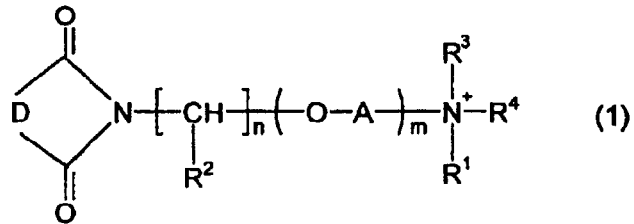

In Column 12, line 6, should appear as follows:

$R^2$ is hydrogen, -CH$_3$ or -OH,

Signed and Sealed this

Twenty-fourth Day of June, 2008

JON W. DUDAS
*Director of the United States Patent and Trademark Office*